United States Patent
Lee et al.

(10) Patent No.: US 10,039,523 B2
(45) Date of Patent: Aug. 7, 2018

(54) HIGH INTENSITY FOCUSED ULTRASOUND PROBES AND METHODS OF MANUFACTURING AND OPERATING THE SAME

(71) Applicant: Samsung Electronics Co., Ltd., Suwon-si (KR)

(72) Inventors: Ho-taik Lee, Yongin-si (KR); Won-chul Bang, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1024 days.

(21) Appl. No.: 14/080,579

(22) Filed: Nov. 14, 2013

(65) Prior Publication Data

US 2014/0236015 A1     Aug. 21, 2014

(30) Foreign Application Priority Data

Feb. 18, 2013   (KR) .......................... 10-2013-0017158

(51) Int. Cl.
*A61B 8/00*      (2006.01)
*A61N 7/02*      (2006.01)
*A61B 90/00*     (2016.01)

(52) U.S. Cl.
CPC .......... *A61B 8/4444* (2013.01); *A61B 8/4455* (2013.01); *A61B 8/4477* (2013.01); *A61N 7/02* (2013.01); *A61B 2090/378* (2016.02); *Y10T 29/49005* (2015.01)

(58) Field of Classification Search
None
See application file for complete search history.

(56) References Cited

U.S. PATENT DOCUMENTS

| | | | | |
|---|---|---|---|---|
| 6,488,626 | B1 * | 12/2002 | Lizzi | A61B 8/0858 600/437 |
| 7,066,887 | B2 | 6/2006 | Flesch et al. | |
| 2008/0167555 | A1 * | 7/2008 | Qian | A61N 7/02 600/439 |
| 2009/0043209 | A1 | 2/2009 | Hirama | |
| 2009/0054772 | A1 | 2/2009 | Lin et al. | |
| 2009/0326372 | A1 * | 12/2009 | Darlington | A61B 8/14 600/439 |
| 2012/0046592 | A1 * | 2/2012 | Albright | A61N 7/02 604/2 |
| 2013/0190623 | A1 * | 7/2013 | Bertolina | A61B 8/4444 600/439 |
| 2014/0024923 | A1 * | 1/2014 | Chapelon | A61N 7/022 600/411 |

FOREIGN PATENT DOCUMENTS

| | | |
|---|---|---|
| JP | 2011-177385 A | 9/2011 |
| KR | 10-2011-0074326 A | 6/2011 |

* cited by examiner

*Primary Examiner* — Jonathan Cwern
(74) *Attorney, Agent, or Firm* — NSIP Law

(57) ABSTRACT

An ultrasound probe includes a therapeutic ultrasound transducer, a slot disposed in the therapeutic ultrasound transducer, and a first diagnostic ultrasound transducer disposed in the slot and configured to move along the slot.

23 Claims, 4 Drawing Sheets

HIGH INTENSITY FOCUSED ULTRASOUND PROBES AND METHODS OF MANUFACTURING AND OPERATING THE SAME

CROSS-REFERENCE TO RELATED APPLICATION

This application claims the benefit under 35 USC 119(a) of Korean Patent Application No. 10-2013-0017158, filed on Feb. 18, 2013, in the Korean Intellectual Property Office, the entire disclosure of which is incorporated herein by reference for all purposes.

BACKGROUND

1. Field

The following description relates to high intensity focused ultrasound (HIFU) probes and methods of manufacturing and operating the same.

2. Description of Related Art

Therapeutic devices for diagnosis and treatment of diseases may be classified as invasive devices and non-invasive devices. Ultrasound probes are one of the non-invasive devices. The ultrasound probes may include diagnostic ultrasound transducers and/or therapeutic ultrasound transducers. High intensity focused ultrasound (HIFU) probes are widely used as therapeutic ultrasound probes. Single plane or bi-plane ultrasound images may be obtained by using the HIFU probes.

However, since currently known HIFU probes are fixed types, the single plane or bi-plane ultrasound images may be obtained only from a certain position and a certain direction by using the currently known HIFU probes. Therefore, it is difficult to increase an accuracy of diagnosis and treatment, and consequently, the diagnosis and treatment may be limited.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, an ultrasound probe includes a therapeutic ultrasound transducer, a slot disposed in the therapeutic ultrasound transducer, and a first diagnostic ultrasound transducer disposed in the slot and configured to move along the slot.

The ultrasound probe may further include a through hole disposed in a center of the therapeutic ultrasound transducer and spaced apart from the slot, and a second diagnostic ultrasound transducer disposed in the through hole. The slot may be disposed between the through hole and an edge of the therapeutic ultrasound transducer.

The slot may include a horizontal component and a vertical component connected to the horizontal component.

The first diagnostic ultrasound transducer may be disposed in the horizontal component and configured to move along the horizontal component, and the ultrasound probe may further include a second diagnostic ultrasound transducer disposed in the vertical component and configured to move along the vertical component.

The slot may include a first slot, and a second slot connected to the first slot and crossing the first slot.

The first diagnostic ultrasound transducer may be disposed in the first slot and configured to move along the first slot, and the ultrasound probe may further include a second diagnostic ultrasound transducer disposed in the second slot and configured to move along the second slot.

The slot may include a first slot, and a second slot spaced apart from the first slot.

The first diagnostic ultrasound transducer may be disposed in the first slot and configured to move along the first slot, and the ultrasound probe may further include a second diagnostic ultrasound transducer disposed in the second slot and configured to move along the second slot.

The second slot may include two slots facing each other with the first slot therebetween.

The first diagnostic ultrasound transducer may be disposed in the first slot and configured to move along the first slot. The ultrasound probe may further include a second diagnostic ultrasound transducer and a third diagnostic ultrasound transducer respectively disposed in the two slots and respectively configured to move along the two slots.

In another general aspect, a method of manufacturing an ultrasound probe including a therapeutic ultrasound transducer and a diagnostic ultrasound transducer, includes forming a slot in the therapeutic ultrasound transducer, and forming the diagnostic ultrasound transducer in the slot so that the diagnostic ultrasound transducer is configured to move along the slot.

The manufacturing method may further include forming a through hole in a center of the therapeutic ultrasound transducer and spaced apart from the slot, and forming another diagnostic ultrasound transducer in the through hole.

The slot may include slots.

The slots may be spaced apart from each other.

In still another general aspect, a method of operating an ultrasound probe including a therapeutic ultrasound transducer and a first diagnostic ultrasound transducer, includes operating the first diagnostic ultrasound transducer, and operating the therapeutic ultrasound transducer. A slot is disposed in the therapeutic ultrasound transducer, and the first diagnostic ultrasound transducer is disposed in the slot and configured to move along the slot.

A through hole may be disposed in a center of the therapeutic ultrasound transducer and spaced apart from the slot, and a second diagnostic ultrasound transducer may be disposed in the through hole.

The slot may include slots. The first diagnostic ultrasound transducer may be disposed in one of the slots, and configured to move along the one of the slots, and other movable diagnostic ultrasound transducers may be disposed in other ones of the slots.

The diagnostic ultrasound transducers included in the other ones of the slots may be operated simultaneously.

The diagnostic ultrasound transducers included in the other ones of the slots may be operated sequentially.

In yet another general aspect, an ultrasound probe includes a first ultrasound transducer configured to treat a subject, and a second ultrasound transducer configured to diagnose the subject, disposed in a surface of the first ultrasound transducer, and configured to move along the surface.

The ultrasound probe may further include a first slot disposed in the first ultrasound transducer, the second ultrasound transducer being disposed in the first slot and configured to move along the first slot.

The ultrasound probe may further include a second slot disposed in the first ultrasound transducer and connected to the first slot, and a third ultrasound transducer configured to diagnose the subject, disposed in the second slot, and configured to move along the second slot.

The surface of the first ultrasound transducer may be concave-curved and have a predetermined radius, and the first slot may have the same curvature as that of the surface.

Other features and aspects will be apparent from the following detailed description, the drawings, and the claims.

Figure 1:
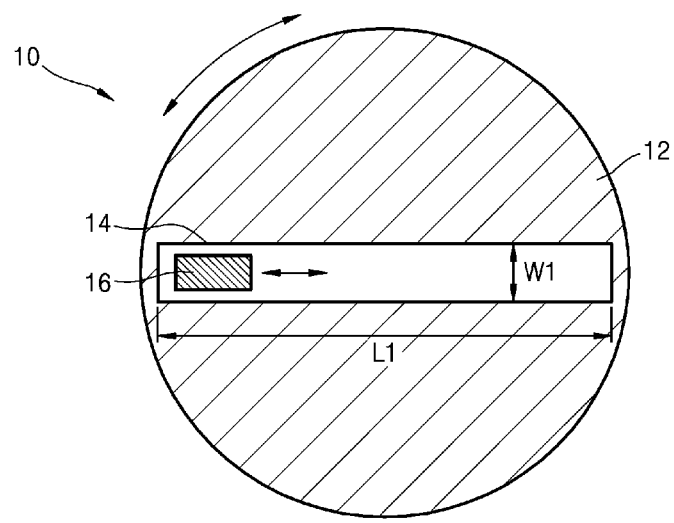
FIG. 1 is a front view illustrating an example of an ultrasound probe according to an embodiment of the present invention.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, an ultrasound probe will be described in detail with reference to the attached drawings. In the drawings, thicknesses of layers and regions are exaggerated for clarity.

FIG. 1 is a front view illustrating an example of an ultrasound probe 10. FIG. 1 is a front view; in other words, a view taken from a direction in which ultrasound is emitted from the ultrasound probe 10. This applies to FIGS. 2 through 6.

Referring to FIG. 1, the ultrasound probe 10 (hereinafter, a first probe 10) includes a first ultrasound transducer 12 and a second ultrasound transducer 16. The first ultrasound transducer 12 may have a circular shape. However, the shape of the first ultrasound transducer 12 may be different. The first ultrasound transducer 12 may be rotated. The first ultrasound transducer 12 is a therapeutic transducer that may be a high intensity focused ultrasound (HIFU) transducer. The first ultrasound transducer 12 includes a slot 14. The slot 14 has a predetermined width W1 and a predetermined length L1. The width W1 of the slot 14 may have a size such that an emission of ultrasound from the second ultrasound transducer 16 may not be interfered. The slot 14 may be formed along a diameter of the first ultrasound transducer 12. Also, the slot 14 may be formed in parallel to the diameter of the first ultrasound transducer 12. The length L1 of the slot 14 is shorter than the diameter of the first ultrasound transducer 12.

The second ultrasound transducer 16 is positioned inside the slot 14. The second ultrasound transducer 16 may be moved along the slot 14. The second ultrasound transducer 16 is a diagnostic transducer. Ultrasound images may be obtained from various positions, for example, from a left side, a center, or a right side of the slot 14, by using the second ultrasound transducer 16. In addition, since the first ultrasound transducer 12 is rotatable, a treatment area, that is, an affected part, may be diagnosed from various positions and directions, whereby improving an accuracy of the diagnosis. Thus, as the accuracy of the diagnosis improves, an accuracy of treatment may also improve.

Figure 2:
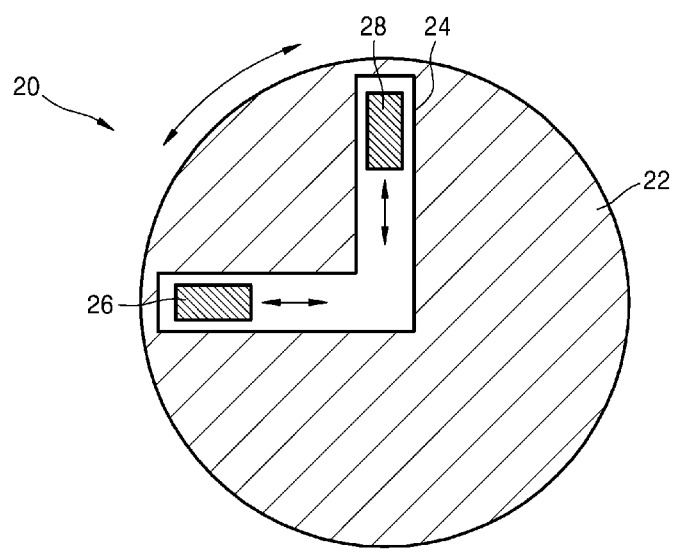
FIGS. 2 through 6 are front views illustrating other examples of an ultrasound probe according to embodiments of the present invention.

FIG. 2 is a front view illustrating another example of an ultrasound probe 20. Referring to FIG. 2, the ultrasound probe 20 (hereinafter, a second probe 20) includes a third ultrasound transducer 22, a fourth ultrasound transducer 26, and a fifth ultrasound transducer 28. The third ultrasound transducer 22 is a therapeutic transducer that may be a HIFU transducer. The third ultrasound transducer 22 may be rotated to a right or left side of the third ultrasound transducer 22. An outer appearance of the third ultrasound transducer 22 may be the same as that of the first ultrasound transducer 12 of FIG. 1. The third ultrasound transducer 22 includes a slot 24 of two directions. The slot 24 includes a vertical component and a horizontal component. The vertical and horizontal components of the slot 24 are formed from a center of the third ultrasound transducer 22 toward respective edges thereof. Viewed from the front view, each of lengths of the vertical and horizontal components of the slot 24 is shorter than a radius of the circular third ultrasound transducer 22.

The fourth and fifth ultrasound transducers 26 and 28 are diagnostic transducers. The fourth ultrasound transducer 26 is provided in the horizontal component of the slot 24. The fifth ultrasound transducer 28 is provided in the vertical component of the slot 24. The fourth ultrasound transducer 26 may be moved left and right along the horizontal component of the slot 24. The fifth ultrasound transducer 28 may be moved up and down along the vertical component of the slot 24. Since the second probe 20 includes the two movable diagnostic fourth and fifth ultrasound transducers 26 and 28, bi-plane ultrasound images may be obtained from various positions and directions by using the fourth and fifth ultrasound transducers 26 and 28. Owing to the rotation of the third ultrasound transducer 22 and the movability of the fourth and fifth ultrasound transducers 26 and 28, an accuracy of diagnosis and treatment of the second probe 20 may be substantially increased compared to the conventional art, and may be higher than that of the first probe 10 of FIG. 1. Also, accurate diagnosis and monitoring of disease may be possible in real time from various positions and directions.

Figure 3:
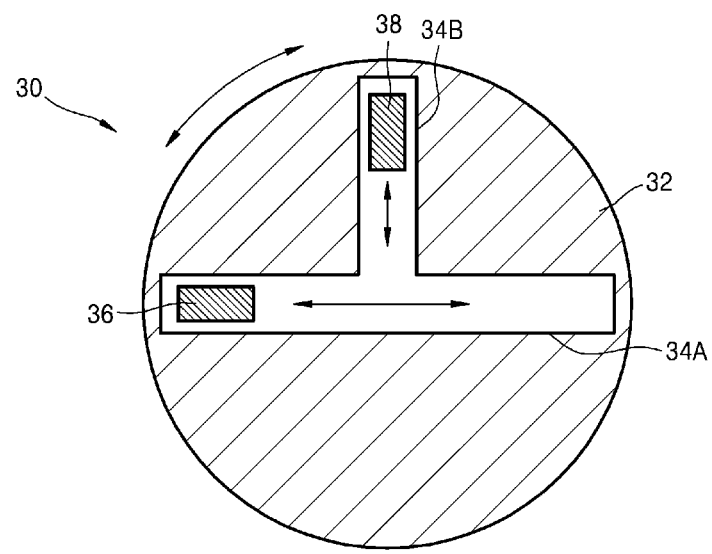

FIG. 3 is a front view illustrating still another example of an ultrasound probe 30. Referring to FIG. 3, the ultrasound probe 30 (hereinafter, a third probe 30) includes a sixth ultrasound transducer 32, a seventh ultrasound transducer 36, and an eighth ultrasound transducer 38. The sixth ultrasound transducer 32 is a therapeutic transducer that may be a HIFU transducer. Although an outer appearance of the sixth ultrasound transducer 32 is a circular shape, the shape may be different. The sixth ultrasound transducer 32 may be rotated clockwise or counterclockwise. The sixth ultrasound transducer 32 includes a first slot 34A and a second slot 34B. The first and second slots 34A and 34B are connected to form a single slot as shown in FIG. 3, but the first and second slots 34A and 34B may be separated from each other. For example, the second slot 34B may be spaced apart from the first slot 34A. The first slot 34A that is a horizontally-formed slot may be the same as or similar to the slot 14 of FIG. 1. For example, a width and a length of the first slot 34A may be the same as or similar to those of the slot 14 of FIG. 1. The second slot 34B may be perpendicular to the first slot 34A. The second slot 34B is formed from a center of the sixth ultrasound transducer 32 toward an edge (a radiation direction) thereof. A length of the second slot 34B is shorter than a radius (a circular radius as viewed from the front view) of the sixth ultrasound transducer 32. A width and the length of the second slot 34B may be the same as or similar to those of the vertical component of the slot 24 of FIG. 2.

The seventh and eighth ultrasound transducers 36 and 38 are diagnostic transducers. The seventh ultrasound transducer 36 is positioned in the first slot 34A and moved along the first slot 34A. The eighth ultrasound transducer 38 is positioned in the second slot 34B and moved along the second slot 34B. The above-described therapeutic sixth ultrasound transducer 32 of the third probe 30 may be rotated, and the diagnostic seventh and eighth ultrasound transducers 36 and 38 may be moved along the slots 34A and 34B, respectively. Thus, the third probe 30 may have the same merits as those of the second probe 20 of FIG. 2 in terms of diagnosis and treatment.

Figure 4:
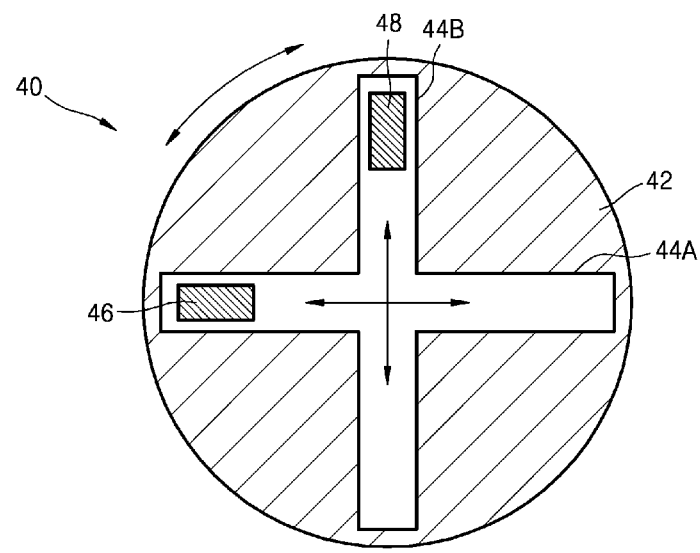

FIG. 4 is a front view illustrating yet another example an ultrasound probe 40. Referring to FIG. 4, the ultrasound probe 40 (hereinafter, a fourth probe 40) includes a ninth ultrasound transducer 42, a tenth ultrasound transducer 46, and an eleventh ultrasound transducer 48. The ninth ultrasound transducer 42 is a therapeutic transducer that may be a HIFU transducer. An outer appearance of the ninth ultrasound transducer 42 may be the same as or similar to that of the sixth ultrasound transducer 32 of FIG. 3. The ninth ultrasound transducer 42 may be rotated clockwise or counterclockwise. The ninth ultrasound transducer 42 includes a third slot 44A and a fourth slot 44B. The third and fourth slots 44A and 44B are connected to each other to form a single slot, and the single slot is in a shape of a cross, as shown in FIG. 4. The third slot 44A may be the same as or similar to the slot 14 of FIG. 1. The fourth slot 44B perpendicularly intersects the third slot 44A. The fourth slot 44B has the same form as the third slot 44A if rotated ninety degrees.

The tenth and eleventh ultrasound transducers 46 and 48 are diagnostic transducers. The tenth ultrasound transducer 46 is provided in the third slot 44A and moved along the third slot 44A. The eleventh ultrasound transducer 48 is provided in the fourth slot 44B and moved along the fourth slot 44B. The tenth and eleventh ultrasound transducers 46 and 48 may be moved simultaneously or sequentially with time lags. Also, the tenth and eleventh ultrasound transducers 46 and 48 may be operated simultaneously or sequentially with time lags. The description regarding the movements and operations of the tenth and eleventh ultrasound transducers 46 and 48 may also be applied to the diagnostic ultrasound transducers of FIGS. 2 and 3. Owing to the rotation of the therapeutic ninth ultrasound transducer 42 and the movement of the diagnostic tenth and eleventh ultrasound transducers 46 and 48, the fourth probe 40 may have the same merits of diagnosis and treatment as those described in relation to FIGS. 2 and 3.

Figure 5:
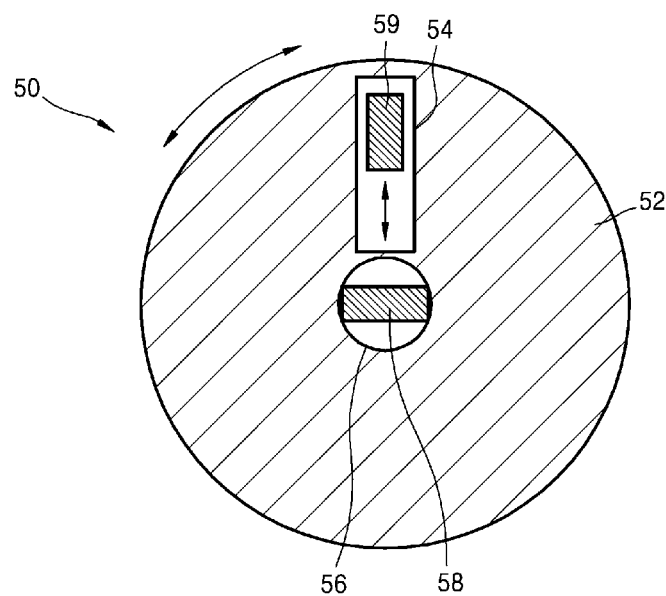

FIG. 5 is a front view illustrating still another example an ultrasound probe 50. Referring to FIG. 5, the ultrasound probe 50 (hereinafter, a fifth probe 50) includes a twelfth ultrasound transducer 52, a thirteenth ultrasound transducer 58, and a fourteenth ultrasound transducer 59. The twelfth ultrasound transducer 52 is a therapeutic transducer that may be a HIFU transducer. An outer appearance of the twelfth ultrasound transducer 52 may be the same as or similar to that of the sixth ultrasound transducer 32 of FIG. 3. The twelfth ultrasound transducer 52 may be rotated clockwise or counterclockwise. The twelfth ultrasound transducer 52 includes a through hole 56 and a fifth slot 54. The through hole 56 is provided in a center of the twelfth ultrasound transducer 52. The fifth slot 54 is disposed between the through hole 56 and an edge of the twelfth ultrasound transducer 52. The fifth slot 54 and the through hole 56 are spaced apart from each other.

The thirteenth and fourteenth ultrasound transducers 58 and 59 are diagnostic transducers. The thirteenth ultrasound transducer 58 is provided in the through hole 56. The fourteenth ultrasound transducer 59 is provided in the fifth slot 54. The thirteenth ultrasound transducer 58 may be fixed to the twelfth ultrasound transducer 52. For example, the thirteenth ultrasound transducer 58 may be fixed to a back side of the twelfth ultrasound transducer 52. If the twelfth ultrasound transducer 52 is rotated, the thirteenth ultrasound transducer 58 and the twelfth ultrasound transducer 52 may be rotated together. The fourteenth ultrasound transducer 59 may be moved along the fifth slot 54. The fifth probe 50 includes the rotatable therapeutic twelfth ultrasound transducer 52, the rotatable thirteenth ultrasound transducer 58, and the movable diagnostic fourteenth ultrasound transducer 59. Thus, the fifth probe 50 may have the same merits of diagnosis and treatment as those described in the previous examples above.

Figure 6:
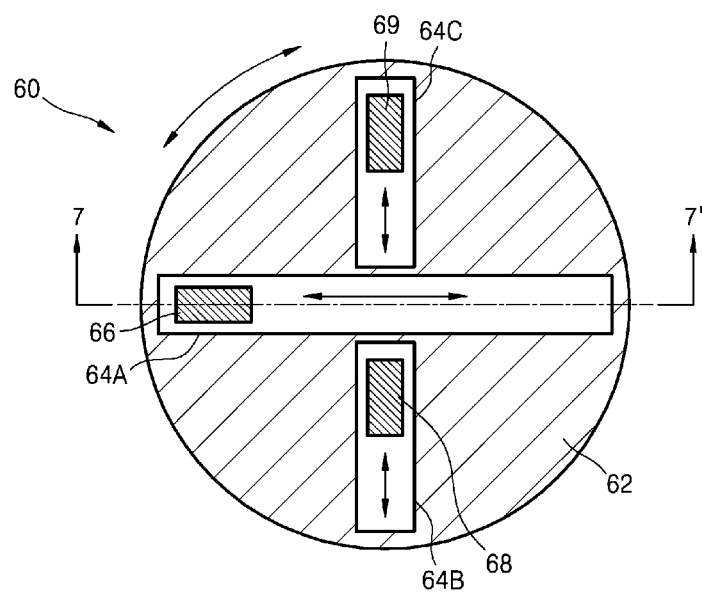

FIG. 6 is a front view illustrating yet another example of an ultrasound probe 60. Referring to FIG. 6, the ultrasound probe 60 (hereinafter, a sixth probe 60) includes a fifteenth ultrasound transducer 62, a sixteenth ultrasound transducer 66, a seventeenth ultrasound transducer 68, and an eighteenth ultrasound transducer 69. The fifteenth ultrasound transducer 62 is a therapeutic ultrasound transducer that may be a HIFU transducer. An outer appearance of the fifteenth ultrasound transducer 62 may be circular, and may be the same as or similar to that of the twelfth ultrasound transducer 52 of FIG. 5. The fifteenth ultrasound transducer 62 may also be rotated clockwise or counterclockwise. The fifteenth ultrasound transducer 62 may include a sixth slot 64A, a seventh slot 64B, and an eighth slot 64C. The sixth slot 64A is spaced apart from the seventh and eighth slots 64B and 64C. The sixth slot 64A is disposed between the seventh and eighth slots 64B and 64C. The seventh and eighth slots 64B and 64C are perpendicular to the sixth slot 64A. The sixth slot 64A may be the same as or similar to the slot 14 of FIG. 1.

The sixteenth through eighteenth ultrasound transducers 66, 68 and 69 are diagnostic transducers. The sixteenth ultrasound transducer 66 is included in the sixth slot 64A, and may be moved along the sixth slot 64A. The seventeenth and eighteenth ultrasound transducers 68 and 69 are respectively provided in the seventh and eighth slots 64B and 64C, and respectively moved along the seventh and eighth slots 64B and 64C.

As described in the examples of FIGS. 1 through 6, an ultrasound probe includes a therapeutic ultrasound transducer that may include a single slot, or two or more slots. Each slot includes a diagnostic ultrasound transducer. Also, the therapeutic ultrasound transducer may further include a through hole. As will be understood from the examples of FIGS. 1 through 6, since one or more slots may be disposed in various ways, the slots may be disposed in various combinations in addition to those described in FIGS. 1 through 6. This means that diagnostic ultrasound transducers may be provided in various ways besides the above-described examples.

Figure 7:
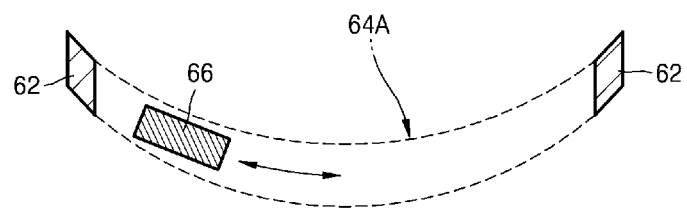
FIG. 7 is a cross-sectional view illustrating the example of the ultrasound probe that is taken along a line 7-7' of FIG. 6.

FIG. 7 is a cross-sectional view illustrating an example of the sixth probe 60 that is taken along a line 7-7' of FIG. 6. Referring to FIG. 7, the fifteenth ultrasound transducer 62 includes a concave-curved surface having a predetermined radius. Considering ultrasound focusing on an affected part or a treatment area, the curved surface of the fifteenth therapeutic ultrasound transducer 62 may be, for example, a paraboloid. The sixth slot 64A may also have the same curvature as that of the surface of the fifteenth ultrasound transducer 62. Since the sixteenth ultrasound transducer 66 in the sixth slot 64A may be moved along the sixth slot 64A, the sixteenth ultrasound transducer 66 may be moved while maintaining the same curvature as that of the surface of the fifteenth ultrasound transducer 62. This example may also be applied to the examples illustrated in FIGS. 1 through 5.

A method of manufacturing an ultrasound probe will now be described. As shown in FIGS. 1 through 6, a single slot or a plurality of slots may be formed in a therapeutic ultrasound transducer. The therapeutic ultrasound transducer may be coupled to a single diagnostic ultrasound transducer or a plurality of diagnostic ultrasound transducers in such a way that the diagnostic ultrasound transducers are formed and movable in respective slots. In the manufacturing method, as shown in FIGS. 1 through 6, the slots may be formed in various shapes and may be separated from each other, and as shown in FIG. 5, the through hole 56 is formed in the center of the therapeutic twelfth ultrasound transducer 52 and spaced apart from the fifth slot 54, and the thirteenth ultrasound transducer 58 is formed in the through hole 56.

A method of operating an ultrasound probe will now be described. For example, the third probe 30 illustrated in FIG. 3 (e.g., a processor of the third probe 30) may initially obtain a bi-plane ultrasound image by operating the diagnostic seventh and eighth ultrasound transducers 36 and 38 simultaneously or sequentially, and may determine a treatment site based on the bi-plane ultrasound image. After accurately identifying the treatment site, the third probe 30 may stop operating the diagnostic seventh and eighth ultrasound transducers 36 and 38, and may operate the therapeutic sixth ultrasound transducer 32 that treats an affected part, that is, a target for treatment. During the treatment, in order to examine a treatment development, the third probe 30 may stop operating the therapeutic sixth ultrasound transducer 32, and may operate the diagnostic seventh and eighth ultrasound transducers 36 and 38 that monitor a treatment status of the affected part. Thereafter, the third probe 30 may stop operating the diagnostic seventh and eighth ultrasound transducers 36 and 38, and may operate the therapeutic sixth ultrasound transducer 32 again to continue the treatment. By repeating the above-described method, optimal treatment results may be obtained. The above-described operation may be applied to operations of the probes of the other examples.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An ultrasound probe comprising:
   a therapeutic ultrasound transducer configured to be rotated;
   a first slot disposed in the therapeutic ultrasound transducer, the first slot comprising a width and a length greater than the width; and
   a first diagnostic ultrasound transducer disposed in the first slot and configured to move along the length of the first slot.

2. The ultrasound probe according to claim 1, further comprising:
   a through hole disposed in a center of the therapeutic ultrasound transducer and spaced apart from the first slot; and
   a second diagnostic ultrasound transducer disposed in the through hole,
   wherein the first slot is disposed between the through hole and an edge of the therapeutic ultrasound transducer.

3. The ultrasound probe according to claim 1, wherein the first slot comprises a horizontal component and a vertical component connected to the horizontal component, the horizontal component and the vertical component each having a respective width and a respective length greater than the respective width.

4. The ultrasound probe according to claim 3, wherein:
   the first diagnostic ultrasound transducer is disposed in the horizontal component and is configured to move along the length of the horizontal component; and
   the ultrasound probe further comprises a second diagnostic ultrasound transducer disposed in the vertical component and configured to move along the length of the vertical component.

5. The ultrasound probe according to claim 1, further comprising:
   a second slot disposed in the therapeutic ultrasound transducer,
   wherein the second slot is connected to the first slot and crosses the first slot.

6. The ultrasound probe according to claim 5, wherein:
   the first diagnostic ultrasound transducer is disposed in the first slot and configured to move along the first slot; and
   the ultrasound probe further comprises a second diagnostic ultrasound transducer disposed in the second slot and configured to move along the second slot.

7. The ultrasound probe according to claim 1, further comprising:
   a second slot spaced apart from the first slot.

8. The ultrasound probe according to claim 7, wherein:
   the first diagnostic ultrasound transducer is disposed in the first slot and configured to move along the length of the first slot; and the ultrasound probe further comprises a second diagnostic ultrasound transducer disposed in the second slot and configured to move along the second slot.

9. The ultrasound probe according to claim 7, further comprising a third slot, wherein the first slot is disposed between the second slot and the third slot, and wherein the second slot and the third slot are each disposed perpendicular to the first slot and are positioned along a same axis of the therapeutic ultrasound transducer.

10. The ultrasound probe according to claim 9, wherein:
the first diagnostic ultrasound transducer is disposed in the first slot and configured to slide along the length of the first slot; and
the ultrasound probe further comprises a second diagnostic ultrasound transducer disposed in the second slot and configured to move along the second slot, and a third diagnostic ultrasound transducer disposed in the third slot and configured to move along the third slot.

11. A method of manufacturing an ultrasound probe comprising a therapeutic ultrasound transducer configured to be rotated and a diagnostic ultrasound transducer, the method comprising:
forming a first slot in the therapeutic ultrasound transducer, the first slot comprising a width and a length greater than the width; and
forming the diagnostic ultrasound transducer in the first slot so that the diagnostic ultrasound transducer is configured to move along the length of the first slot.

12. The manufacturing method of claim 11, further comprising:
forming a though hole in a center of the therapeutic ultrasound transducer and spaced apart from the first slot; and
forming another diagnostic ultrasound transducer in the through hole.

13. The manufacturing method of claim 11, further comprising:
forming a second slot in the therapeutic ultrasound transducer.

14. The manufacturing method of claim 13, wherein the first slot and the second slot are spaced apart from each other.

15. A method of operating an ultrasound probe comprising a therapeutic ultrasound transducer configured to be rotated and a first diagnostic ultrasound transducer, the method comprising:
operating the first diagnostic ultrasound transducer; and
operating the therapeutic ultrasound transducer by rotating the therapeutic ultrasound transducer,
wherein a first slot is disposed in the therapeutic ultrasound transducer, the first slot comprising a width and a length greater than the width, and the first diagnostic ultrasound transducer is disposed in the first slot, and
wherein the operating of the first diagnostic ultrasound transducer comprises moving the first diagnostic ultrasound transducer along the length of the first slot.

16. The operating method of claim 15, further comprising:
operating a second diagnostic ultrasound transducer disposed in a through hole,
wherein the through hole is disposed in a center of the therapeutic ultrasound transducer and spaced apart from the first slot.

17. The operating method of claim 15, further comprising:
operating a second diagnostic ultrasound transducer disposed in a second slot, wherein the second slot is disposed in the therapeutic ultrasound transducer.

18. The operating method of claim 17, further comprising operating the first diagnostic ultrasound transducer and the second diagnostic ultrasound transducer simultaneously.

19. The operating method of claim 17, further comprising operating the first diagnostic ultrasound transducer and the second diagnostic ultrasound transducer sequentially.

20. An ultrasound probe comprising:
a first ultrasound transducer configured to treat a subject; and
a second ultrasound transducer configured to diagnose the subject, disposed in a first slot extending along a surface of the first ultrasound transducer, and configured to slide along the surface within the first slot.

21. The ultrasound probe of claim 20, wherein:
the first slot comprises a width and a length greater than the width,
wherein the second ultrasound transducer is disposed in the first slot and is configured to move along the length of the first slot.

22. The ultrasound probe of claim 21, further comprising:
a second slot disposed in the first ultrasound transducer and connected to the first slot; and
a third ultrasound transducer configured to diagnose the subject, disposed in the second slot, and configured to move along the second slot.

23. The ultrasound probe of claim 21, wherein:
the surface of the first ultrasound transducer is concave-curved and has a predetermined radius; and
the first slot has the same curvature as that of the surface.

* * * * *